United States Patent [19]

Monkovic et al.

[11] Patent Number: 4,507,485

[45] Date of Patent: Mar. 26, 1985

[54] 3,4-DISUBSTITUTED-1,2,5-OXADIAZOLES HAVING HISTAMINE $H_2$-RECEPTOR ANTAGONIST ACTIVITY

[75] Inventors: Ivo Monkovic, Fayetteville; Ronnie R. Crenshaw, Dewitt, both of N.Y.

[73] Assignee: Bristol-Myers Company, New York, N.Y.

[21] Appl. No.: 573,258

[22] Filed: Jan. 23, 1984

[51] Int. Cl.³ .................. C07D 271/08; C07D 413/06; C07D 413/12

[52] U.S. Cl. .................................. 546/210; 548/125; 546/277; 544/367; 544/360; 544/137; 544/124; 544/60

[58] Field of Search ................ 548/125; 546/277, 210; 544/367, 360, 137, 124, 60; 424/263, 267, 269, 246, 248.51, 248.56

[56] References Cited

U.S. PATENT DOCUMENTS 3,594,388 7/1971 Lehmann et al. .................. 548/125

OTHER PUBLICATIONS

Ganellin et al., Federation Proceedings, vol. 35, pp. 1924–1930.
Drugs of the Future, vol. 1, No. 1, (1976), pp. 13–18.

Primary Examiner—Robert T. Bond
Attorney, Agent, or Firm—Richard R. Lloyd

[57] ABSTRACT

Histamine $H_2$-antagonists of the formula:

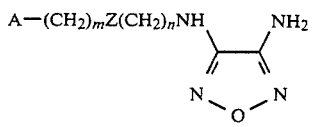

wherein
m is an integer of from 0 to 2 inclusive;
n is an integer of from 2 to 5 inclusive;
Z is oxygen, sulfur or methylene; and
A is

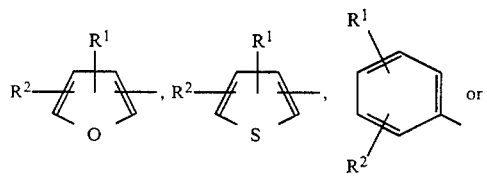

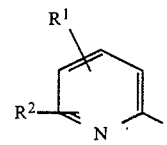

in which $R^1$ is hydrogen, (lower)alkyl, or (lower)alkoxy, and $R^2$ is

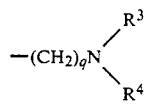

in which q is an integer of from 1 to 4 inclusive, and $R^3$ and $R^4$ each are independently, (lower)alkyl, (lower)alkoxy(lower)alkyl in which the (lower)alkoxy moiety is at least two carbon atoms removed from the nitrogen atom, cyclo(lower)alkyl, or phenyl(lower)alkyl; provided that $R^3$ and $R^4$ may not both be cyclo(lower)alkyl; or $R^3$ and $R^4$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, or 3-azabicyclo[3.2.2]non-3-yl; and nontoxic, pharmaceutically acceptable salts, hydrates, solvates and N-oxides thereof.

7 Claims, No Drawings

3,4-DISUBSTITUTED-1,2,5-OXADIAZOLES HAVING HISTAMINE H₂-RECEPTOR ANTAGONIST ACTIVITY

SUMMARY OF THE INVENTION

Certain 3,4-disubstituted-1,2,5-oxadiazoles having the formula:

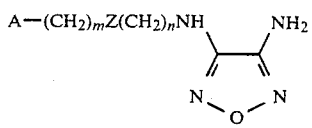

wherein A, m, Z and n are as defined below, and their nontoxic pharmaceutically acceptable salts, hydrates, solvates and N-oxides, are potent histamine $H_2$-receptor antagonists which inhibit gastric acid secretion and are useful in the treatment of peptic ulcers and other pathological hypersecretory conditions.

BACKGROUND AND PRIOR ART

Burimamide (IIa) was the first clinically effective histamine $H_2$-receptor antagonist. It inhibits gastric secretion in animals, including man, but oral absorption is poor.

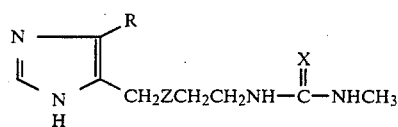

| | | | |
|---|---|---|---|
| IIa; R = H, | Z = CH₂, | X = S | Burimamide |
| b; R = CH₃, | Z = S, | X = S | Metiamide |
| c; R = CH₃, | Z = S, | X = NCN | Cimetidine |

Metiamide (IIb), a subsequently evaluated histamine $H_2$-antagonist, is more potent than burimamide and is orally active in man. Clinical utility was limited, however, owing to toxicity (agranulocytosis). Cimetidine (IIc) is as effective an histamine $H_2$-antagonist as metiamide, without producing agranulocytosis, and has recently been marketed as an anti-ulcer drug.

Reviews on the development of histamine $H_2$-antagonists, including those discussed in the preceding paragraph, may be found in C. R. Ganellin, et al., *Federation Proceedings*, 35, 1924 (1976), in *Drugs of the Future*, 1, 13 (1976) and in references cited therein.

U.S. application Ser. No. 473,791, filed Mar. 16, 1983 discloses 3,4-disubstituted-1,2,5-thiadiazoles having the formula:

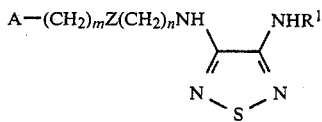

and processes for their preparation, wherein the variables A, m, Z and n are similar to the corresponding substituents of the compounds disclosed and claimed herein and wherein $R^1$ may be hydrogen. However, the compounds disclosed therein are thiadiazoles, not oxadiazoles as described and claimed herein.

COMPLETE DESCRIPTION

This invention relates to histamine $H_2$-antagonists which are effective inhibitors of gastric acid secretion in animals, including man, which are useful in the treatment of peptic ulcers and other conditions caused or exacerbated by gastric acidity, and which have the formula:

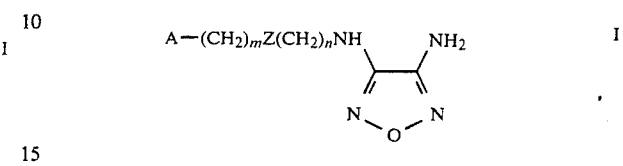

wherein
  m is an integer of from 0 to 2 inclusive;
  n is an integer of from 2 to 5 inclusive;
  Z is oxygen, sulfur or methylene; and
  A is

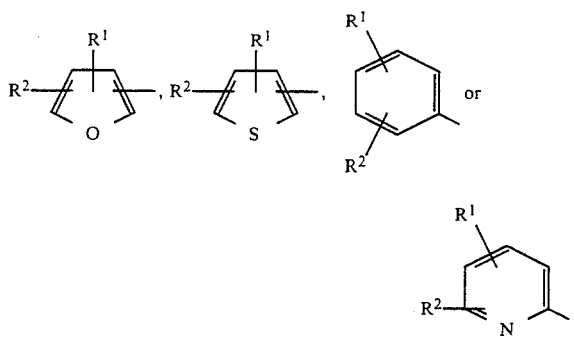

in which $R^1$ is hydrogen, (lower)alkyl, or (lower)alkoxy, and $R^2$ is

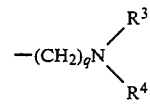

in which q is an integer of from 1 to 4 inclusive, and $R^3$ and $R^4$ each are independently, (lower)alkyl, (lower)alkoxy (lower)alkyl in which the (lower)alkoxy moiety is at least two carbon atoms removed from the nitrogen atom, cyclo(lower)alkyl, or phenyl(lower)alkyl; provided that $R^3$ and $R^4$ may not both be cyclo(lower)alkyl; or $R^3$ and $R^4$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, or 3-azabicyclo[3.2.2]non-3-yl; and nontoxic, pharmaceutically acceptable salts, hydrates, solvates and N-oxides thereof.

This invention also relates to processes for the preparation of the compounds of Formula I and to intermediates useful in the preparation of the compounds of Formula I.

The present invention includes within its scope all possible tautomeric forms, geometric isomers and optical isomers of the compounds of Formula I, as well as mixtures thereof.

As used herein and in the claims, the term "lower" when used in conjunction with the terms "(lower)alkyl", "(lower)alkoxy", "phenyl(lower)alkyl" and "(lower)alkoxy(lower)alkyl" means straight or branched chain groups containing from 1 to 6 carbon atoms. Preferably these groups contain from 1 to 4 carbon atoms and, most preferably, they contain 1 to 2 carbon atoms. The term "cyclo(lower)alkyl" means a cycloalkyl group containing from 3 to 6 carbon atoms. The term "nontoxic pharmaceutically acceptable salts" is intended to include salts of the compounds of Formula I with any nontoxic pharmaceutically acceptable acid. Such acids are wellknown and include hydrochloric, hydrobromic, sulfuric, sulfamic, phosphoric, nitric, maleic, fumaric, succinic, oxalic, benzoic, methanesulfonic, tartaric, citric, camphorsulfonic, levulinic and the like. The salts are made by methods known in the art.

In the compounds of Formula I, substituent A preferably is piperidinomethylphenyl or dimethylaminomethylfuryl. Substituent Z preferably is sulfur or oxygen. It is preferred that m is zero or 1 and n is 2 or 3.

As presently envisaged, the most preferred compounds of Formula I are:

(1) 3-amino-4-[3-(3-piperidinomethylphenoxy)-propylamino]-1,2,5-oxadiazole; and (2) 3-amino-4-{2-[(5-dimethylaminomethyl-2-furyl)-methylthio]ethylamino}-1,2,5-oxadiazole; and their nontoxic, pharamaceutically acceptable salts, hydrates and solvates.

The compounds of Formula I may be prepared by various reaction schemes.

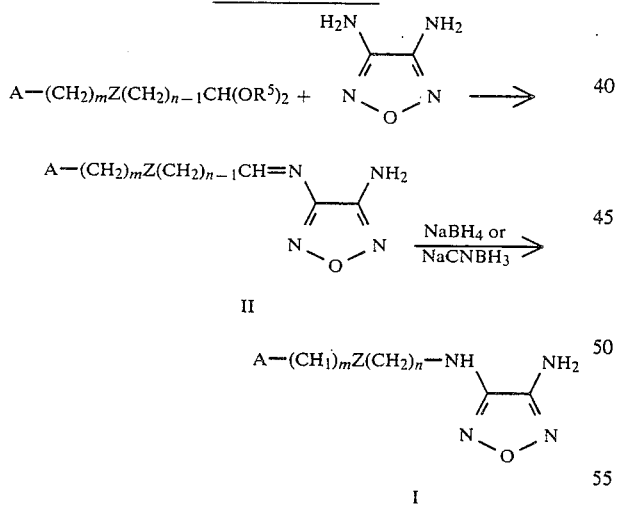

in which $R^5$ is a (lower)alkyl group such as ethyl.

The compound of Formula II may also be prepared by the following reaction scheme:

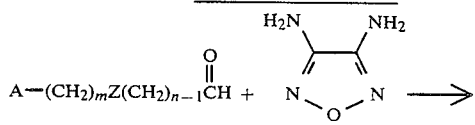

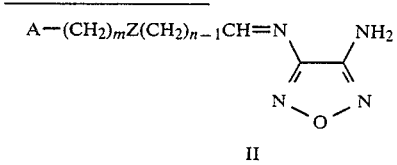

The reactions are conducted in an inert solvent such as N,N-dimethylformamide (DMF), N,N-dimethylacetamide (DMA), dimethyl sulfoxide (DMSO) or tetrahydrofuran (THF). It is preferred to conduct the reactions at a temperature of from $-20°$ C. to $100°$ C. The preferred reaction temperature is room temperature. The reaction to form the compound of Formula II is preferably conducted in the presence of a Lewis acid such as boron trifluoride etherate.

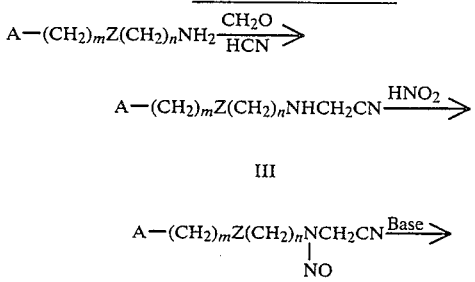

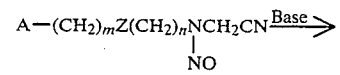

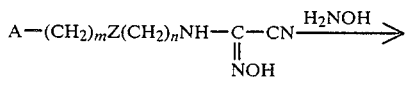

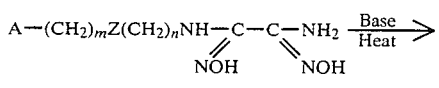

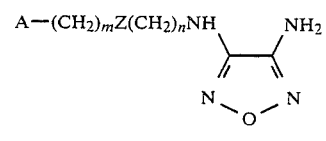

The reactions may generally be conducted at a temperature ranging from room temperature to $100°$ C., except for the last step which should be conducted at a temperature of from $100°$ C. to $300°$ C. The reactions are conducted in an inert solvent.

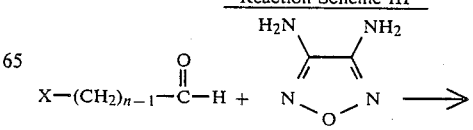

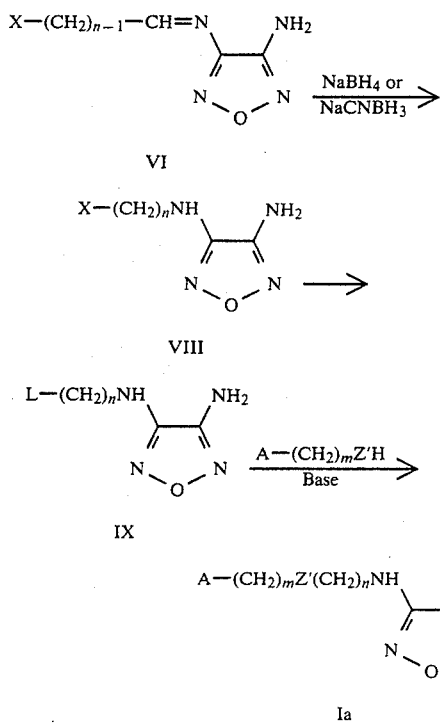

in which X is hydroxy, a protected hydroxy group, e.g., t-butoxy, acetoxy, benzoyloxy, etc., or a halo group. The substituent L is a good leaving group such as halo, e.g., chloro, bromo, iodo, or sulfonyloxy, e.g., methanesulfonyloxy, p-toluenesulfonyloxy or the like. Suitable leaving groups are well known in the art. The conversion of X to L is a conventional procedure. It will be understood that L may be the same as X in which case the step going from the compound of Formula VIII to the compound of Formula IX will be omitted. The substituent Z' is oxygen or sulfur. Examples of compounds A—$(CH_2)_m$Z'H include 3-piperidinomethylphenol and 5-[(dimethylamino)methyl]-2-furanmethylthiol. All of the reactions may be conducted in inert solvents at temperatures ranging from 0° C. to 100° C.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed (and the number of times to be administered per day) is within the discretion of the physician, and may be varied by titration of the dosage to the particular circumstances of the specific patient. With the preferred compounds of this invention, each oral dosage unit will contain the active ingredient in an amount of from about 2 mg to about 300 mg, and most preferably from about 4 mg to about 100 mg. The active ingredient will preferably be administered in equal doses from one to four times a day.

Histamine $H_2$-receptor antagonists have been shown to be effective inhibitors of gastric secretion in animals and man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al, *Lancet*, 1, 8001 (1977). One of the preferred compounds of this invention has been compared with cimetidine in various tests and has been found to be more potent that cimetidine as a histamine $H_2$-receptor antagonist as shown in Table 1.

DETERMINATION OF GASTRIC ANTISECRETORY ACTIVITY IN THE GASTRIC FISTULA RAT

Male Long Evans rats weighing about 240-260 grams at the time of cannula implantation are used. The design and implantation of the stainless steel cannula into the anterior wall of the fore-stomach are carried out essentially as described by Pare et al, *Laboratory Animal Science*, 27, 244 (1977). The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30-40 ml of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way, the rat is not restricted and can move freely about the cage during collection periods. The remainder of the assay is carried out as described by Ridley et al., *Research Comm. Chem. Path. Pharm.*, 17, 365 (1977).

Gastric secretions collected during the first hour after washing the stomach are discarded as they may be contaminated. For oral evaluation, the catheter is then removed from the cannula and replaced with the plugging screw. Water (2 ml/kg) is administered orally via gastric intubation and the animal is returned to the cage for 45 minutes. After this time the plugging screw is removed and replaced with a catheter to which a small plastic vial has been attached to collect the gastric secretions. A two-hour sample is collected (this represents the control secretion), the catheter is removed and replaced with the plugging screw. The test drug is now administered orally in a volume of 2 ml/kg via gastric intubation. Forty-five minutes later the plugging screw is again removed, replaced with the catheter attached to a small plastic vial and another 2-hour sample is collected. The secretions in the second sample are compared to those of the control sample in order to determine the effects of the test drug.

When test compounds are to be evaluated parenterally, the animal is injected ip or sc with the test compound vehicle in a volume of 2 ml/kg immediately after discarding the initial 60-minute collection. A two-hour sample is collected (control secretion) and the animals are injected either ip or sc with the test compound in a volume of 2 ml/kg. An additional two-hour sample is collected and its secretions are compared to those of the control period to determine drug effects.

The samples are centrifuged and placed in a graduated centrifuge tube for volume determination. Titratable acidity is measured by titrating a one-ml sample to pH 7.0 with 0.02N NaOH, using an Autoburet and an electrometric pH meter (Radiometer). Titratable acid output is calculated in microequivalents by multiplying the volume is milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for determination of a dose response curve.

TABLE 1

| Gastric Antisecretory Activity In The Gastric Fistula Rat | | |
|---|---|---|
| Compound | $ED_{50}$ sc μmoles/kg | Potency Ratio |
| cimetidine | 3.48 | 1.0 |
| Example 1 | 0.18 | 19.3 |
| Example 2 | 5.0 | 0.70 |

DETERMINATION OF GASTRIC ANTISECRETORY ACTIVITY IN THE HEIDENHAIN POUCH DOG

Prior to surgery, hematology and blood chemistry profiles are obtained and an assessment made as to the general health of selected female dogs. Dogs are vaccinated with Tissue Vax 5 (DHLP—Pitman-Moore) and housed in general animal quarters for four weeks' observation so incipient diseases may become apparent. Dogs are fasted with water ad libitum 24 hours prior to surgery.

Anesthesia is induced with Sodium Pentothal (Abbott) 25-30 mg/kg iv. Subsequent anesthesia is maintained with methoxyflurane (Pitman-Moore). A midline linea alba incision from xiphoid to umbilicus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon or Delrin with dimensions and attachments after DeVito and Harkins (*J. Appl. Physiol.*, 14, 138 (1959). Post operatively, dogs are medicated with antibiotics and an analgesic. They are allowed 2-3 months for recovery. Experiments are carried out in the following way: Dogs are fasted overnight (~18 hours) with water ad libitum prior to each experiment. The dogs are placed in a sling and a saphenous vein cannulated for drug administration. Histamine as the base (100 μg/kg/hr) and chlorpheniramine maleate (0.25 mg/kg/hr) are infused continuously (in a volume of 6 ml/hr) with a Harvard infusion pump.

Ninety minutes' infusion are allowed for the dogs to reach a steady state of acid output. At this time the drug or normal saline (control) is administered concomitantly with the secretagogue in a volume of 0.5 ml/kg over a 30 second period. When oral studies are to be carried out, the drug is administered via gastric gavage in a volume of 5 ml/kg. Infusion of the secretagogue is continued and 15 minute samples of the gastric juice are taken for 4.5 hours. Each sample is measured to the nearest 0.5 ml and titratable acidity is determined by titrating a 1 ml sample to pH 7.0 with 0.2N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings and the response is the average for five days at that dose level.

TABLE 2

| Gastric Antisecretory Activity In The Heindenhain Pouch Dog | | |
|---|---|---|
| Compound | $ED_{50}$ iv mg/kg | Potency Ratio |
| Ranitidine | 0.054 | 1.0 |
| Example 1 | 0.03 | 1.8 |

EXAMPLE 1

A. β-(3-Piperidinomethylphenoxy)propionaldehydediethyl acetal

To a stirred suspension of sodium hydride (2.5 g of 55%, 57 mmoles, washed with n-pentane) in dimethylformamide (60 ml) was added in several portions 3-piperidinomethylphenol (9.56 g, 50 mmoles). After stirring for 15 minutes, β-chloropropionaldehyde diethyl acetal (8.4 g, 50 mmoles) was added and the mixture was heated to 100°-105° C. for 30 minutes. After cooling the mixture was partitioned between water and a 1:3 mixture of ether and n-pentane (100 ml). The organic phase was washed with 1N NaOH (2×20 ml), water, brine and then filtered over anhydrous sodium sulfate and concentrated in vacuo to give 13.2 g (82.5%) of the title compound as a colorless oil.

Anal. Calc'd for $C_{19}H_{31}NO_3$: C, 70:99; H, 9.72; N,4.36. Found: C, 71.65; H, 9.93; N,4.38.

B. 3-Amino-4-[3-(3-piperidinomethylphenoxy)-propylamino]-1,2,5-oxadiazole

To a cooled (ice-water) stirred solution of the diethyl acetal prepared in step A (3.21 g, 10 mmoles) and 3,4-diamino-1,2,5-oxadiazole (1 g, 10 mmoles) [prepared according to J. Org. Chem., 40,2744 (1975)] in 30 ml of dry tetrahydrofuran and 30 mg of methanol in a 250 ml 3-neck round bottom flask was added dropwise over a period of 15 minutes boron trifluoride etherate (2.46 ml, 2.838 g, 20 mmoles) under argon. The stirring was continued for 40 min at ambient temperature followed by the addition of sodium cyanoborohydride (1.256 g, 20 mmoles) in several portions, causing exothermic reaction with evolution of gas. The mixture was stirred for 1 hour followed by acidification with ice-cold 2N hydrochloric acid (20 ml). After stirring for 10 minutes the mixture was made basic by the addition of 2N sodium hydroxide (40 ml) and extracted with ether-n-pentane (200 ml, 1:1). The extract was shaken with 1N sodium hydroxide (3×5 ml), water, brine and filtered over anhydrous sodium sulfate. The aqueous layer and washings were combined and extracted with another portion of ether-n-pentane (200 ml, 1:1) and the extract was processed as above. The extracts were combined and concentrated in vacuo to give 1.88 g of crude product as a colorless oil. This was purified by chromatography on alumina column using $CH_2Cl_2(100)$: $—CH_3OH(1.2)$ as the mobile phase. The appropriate fractions gave 710 mg of purified title compound as an oil. Further purification was achieved by chromatography on silica using $CH_2Cl_2(100):CH_3OH(2):NH_4OH(0.2)$ as the mobile phase. The appropriate fractions yielded 556 mg of the title compound as a white solid, mp 87°–88° C.

Anal. Calc'd for $C_{17}H_{25}N_5O_2$: C, 61.60; H, 7.60; N, 21.13. Found: C, 61.75; H, 7.70; N, 21.19.

EXAMPLE 2

A. 5[(Dimethylamino)methyl]-2-furanmethanethioacetaldehyde diethyl acetal

To a stirred suspension of sodium hydride (2.75% g, of 50%, 53.6 mmoles, washed with n-pentane) in dimethylformamide (70 ml) was added in several portions 5-[(dimethylamino)methyl]-2-furanamethanethiol oxalate (3.5 g, 13.41 mmoles) [prepared according to U.K. Patent Application No. 2067991]. The mixture was stirred 15 minutes followed by the addition of a solution of bromoacetaldehyde diethyl acetal (2.883 g, 14.6 mmole) in dimethylformamide (15 ml). The mixture was stirred for 2 hrs followed by a partition between ether and water. The organic phase was washed with water then extracted with 0.25N ice-cold hydrochloric acid (60 ml). The extract was basified as soon as possible with sodium carbonate and extracted with ether to give, after drying and concentration in vacuo 3.78 g of the title product. A sample for analysis distilled at 106°–109° C./0.04 mm.

Anal. Calc'd for $C_{14}H_{25}NO_3S$: C, 58.50; H, 8.77; N, 4.87; S, 11.15. Found: C, 58.03; H, 8.68; N, 4.79; S, 11.24.

B. 3-Amino-4-{2-[(5-dimethylaminomethyl-2-furyl)-methylthio]ethylamino}-1,2,5-oxadiazole 5-[(Dimethylamino)methyl]-2-furanmethanethioacetaldehyde diethyl acetal (3.6 g, 12,54 mmoles) [prepared in step A] was dissolved in 1N hydrochloric acid (55 ml) and the solution allowed to stand at ambient temperature for 10 minutes, followed by basification with sodium carbonate and extraction with toluene (2×60 ml). The extract was dried over sodium sulfate and filtered. To the filtrate was added 3,4-diamino-1,2,5-oxadiazole (1.5 g, 15 mmoles) and the mixture was heated to reflux under azeotropic conditions for 10 minutes, followed by concentration in vacuo to a volume of about 15 ml and heated under reflux for another 10 minutes. After cooling, to the mixture was added a solution of sodium borohydride (750 mg) in absolute ethanol (30 ml), and the whole heated under reflux for 15 minutes, cooled, acidified with 1N hydrochloric acid, and after stirring at ambient temperature for 10 minutes, basified with sodium carbonate and extracted with ether. The extract was dried and concentrated in vacuo to give crude product. This was purified by chromatography on silica using $CH_2Cl_2(100):CH_3OH(5):NH_4OH(1)$ as the mobile phase. Further purification was achieved by preparation high pressure liquid chromatography on silica using $CH_2Cl_2(100):2C_3H_7OH(10):NH_4OH(0.5)$ as the mobile phase. The appropriate fractions yielded the title compound as an oil, mass spec. MW=297.

Anal. Calc'd for $C_{12}H_{19}N_5O_2S$: C, 48.48; H, 6.40; N, 23.57; S, 10.77. Found: C, 47.68; H, 6.70; N, 21.07; S, 10.40.

EXAMPLE 3

The general procedure of Example 1, Step A and B is repeated except that the 3-piperidinomethylphenol utilized therein is replaced by an equimolar amount of:
(a) 3-pyrrolidinomethylphenol,
(b) 3-dimethylaminoethylphenol,
(c) 3-dimethylaminomethylphenol,
(d) 3-(2-methylpyrrolidino)methylphenol,
(e) 3-(3-methylpyrrolidino)methylphenol,
(f) 3-(4-methylpyperidino)methylphenol,
(g) 3-morpholinomethylphenol,
(h) 3-(n-methylpiperazino)methylphenol,
(i) 3-(1,2,3,6-tetrahydro-1-pyridyl)methylphenol,
(j) 3-hexamethyleneiminomethylphenol,
(k) 3-heptamethyleneiminomethylphenol and
(l) 3-(3-azabicyclo[3.2.2]non-3-y)methylphenol
and there is thereby produced:
(a) 3-amino-4-[3-(3-pyrrolidinomethylphenoxy)propylamino]-1,2,5-oxadiazole,
(b) 3-amino-4-[3-(3-dimethylaminomethylphenoxy)-propylamino]-1,2,5-oxadiazole,
(c) 3-amino-4-[3-(3-diethylaminomethylphenoxy)-propylamino]-1,2,5-oxadiazole,
(d) 3-amino-4-{3-[3-(2-methylpyrrolidino)methylphenoxy]propylamino}-1,2,5-oxadiazole,
(e) 3-amino-4-{3-[3-(3-methylpyrrolidino)methylphenoxy]propylamino}-1,2,5-oxadiazole,
(f) 3-amino-4-{3-[3-(4-methylpyrrolidino)methylphenoxy]propylamino-}1,2,5-oxadiazole,
(g) 3-amino-4-[3-(3-morpholinomethylphenoxy)-propylamino]-1,2,5-oxadiazole,
(h) 3-amino-4-{3-[3-(m-methylpiperazino)methylphenoxy]propylamino}-1,2,5-oxadiazole,
(i) 3-amino-4-{3-[3-(1,2,3,6-tetrahydro-1-pyridyl)methylphenoxy]propylamino)-1,2,5-oxadiazole,
(j) 3-amino-4-[3-(3-hexamethyleneiminomethylphenoxy)propylamino]-1,2,5-oxadiazole,
(k) 3-amino-4-[3-(3-heptamethyleneiminomethylphenoxy)propylamino]-1,2,5-oxadiazole, and
(l) 3-amino-4-{3-[3-(3-azabicyclo[3.2.2]non-3-yl)methylphenoxy]propylamino}-1,2,5-oxadiazole.

EXAMPLE 4

The general procedure of Example 2, Step A and B is repeated except that the 5-[(dimethylamino)methyl]-2-furanmethanethiol utilized therein is replaced by an equimolar amount of 2-[(dimethylamino)methyl]-4-thiophenemethanethiol to give 3-amino-4-{2-[(5-dimethylaminomethyl-3-thienyl)methylthio}ethylamino)-1,2,5-oxadiazole.

What is claimed is:

1. A compound of the formula

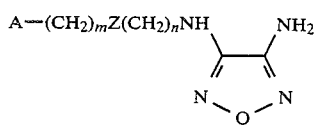

wherein m is an integer of from 0 to 2 inclusive;

n is an integer of from 2 to 5 inclusive;

Z is oxygen, sulfur or methylene; and

A is

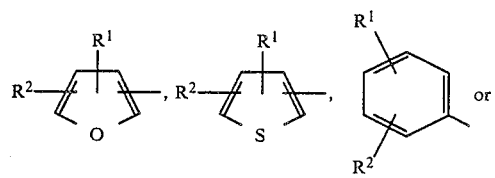

in which $R^1$ is hydrogen, (lower)alkyl, or (lower)alkoxy, and $R^2$ is

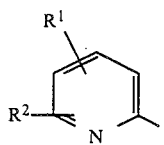

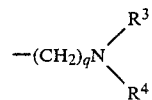

in which q is an integer of from 1 to 4 inclusive, and $R^3$ and $R^4$ each are independently, (lower)alkyl, (lower)alkoxy(lower)alkyl in which the (lower)alkoxy moiety is at least two carbon atoms removed from the nitrogen atom, cyclo(lower)alkyl, or phenyl(lower)alkyl; provided that $R^3$ and $R^4$ may not both be cyclo(lower)alkyl; or $R^3$ and $R^4$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, or 3-azabicyclo[3.2.2]non-3-yl; and nontoxic, pharmaceutically acceptable salts, hydrates, solvates and N-oxides thereof.

2. A compound of claim 1 wherein substitutent A is piperidinomethylphenyl or dimethylaminomethylfuryl.

3. A compound of claim 2 wherein substituent Z is sulfur or oxygen.

4. A compound of claim 3 wherein m is 0 or 1.

5. A compound of claim 4 wherein n is 2 or 3.

6. The compound of claim 5 which is 3-amino-4-[3-(3-piperidinomethylphenoxy)propylamino]-1,2,5-oxadiazole and its nontoxic, pharmaceutically acceptable salts, hydrates and solvates.

7. The compound of claim 5 which is 3-amino-4-{2-[(5-dimethylaminomethyl-2-furyl)-methylthio]ethylamino}-1,2,5-oxadiazole; and its nontoxic, pharmaceutically acceptable salts, hydrates and solvates.

* * * * *